United States Patent [19]
Oong et al.

[11] Patent Number: 5,168,162
[45] Date of Patent: *Dec. 1, 1992

[54] METHOD OF DETECTING THE PRESENCE OF ANOMALIES IN EXFOLIATED CELLS USING INFRARED SPECTROSCOPY

[75] Inventors: Patrick T. T. Oong, Ottawa, Canada; Basil Rigas, White Plains, N.Y.

[73] Assignees: Cornell Research Foundation, Inc., Ithaca, N.Y.; National Research Council of Canada, Ottawa, Canada

[*] Notice: The portion of the term of this patent subsequent to Aug. 6, 2008 has been disclaimed.

[21] Appl. No.: 656,508

[22] Filed: Feb. 19, 1991

[51] Int. Cl.⁵ .................................. G01N 21/35
[52] U.S. Cl. ........................ 250/339; 250/341; 128/664
[58] Field of Search ............... 250/339, 341; 128/664

[56] References Cited

U.S. PATENT DOCUMENTS

| | | | |
|---|---|---|---|
| 3,267,932 | 8/1966 | Valliere | 128/675 |
| 3,279,460 | 10/1966 | Sheldon | 128/6 |
| 3,327,119 | 6/1967 | Kamentsky | 250/461.2 |
| 3,456,641 | 7/1969 | Yokota et al. | 128/4 |
| 3,497,690 | 2/1970 | Wheeless, Jr. et al. | 250/461.2 |
| 3,877,818 | 4/1975 | Button et al. | 356/416 |
| 4,017,192 | 4/1977 | Rosenthal | 356/39 |
| 4,063,892 | 12/1977 | Vassilev et al. | 436/64 |
| 4,102,646 | 7/1978 | Sleeter | 250/338.1 |
| 4,247,773 | 1/1981 | Nexo | 250/339 |
| 4,273,442 | 6/1981 | Lubbers | 356/326 |
| 4,447,725 | 5/1984 | Biggs | 250/339 |
| 4,481,418 | 11/1984 | Vanzetti | 250/338.1 |
| 4,515,165 | 5/1985 | Carroll | 128/664 |
| 4,623,793 | 11/1986 | Hofke | 250/341 |
| 4,633,087 | 12/1986 | Rosenthal | 250/341 |
| 4,642,778 | 2/1987 | Hieftje et al. | 364/498 |
| 4,649,275 | 3/1987 | Nelson et al. | 250/358.1 |
| 4,707,605 | 11/1987 | Astheimer et al. | 250/347 |
| 4,767,717 | 8/1988 | Baisden | 436/64 |
| 4,767,928 | 8/1988 | Nelson | 250/341 |
| 4,771,176 | 9/1988 | Schiefer | 250/339 |
| 4,807,637 | 2/1989 | Bjorkholm | 128/664 |
| 4,831,258 | 5/1989 | Paulk | 250/349 |
| 5,038,039 | 8/1991 | Wong et al. | 250/341 |

FOREIGN PATENT DOCUMENTS

| | | | |
|---|---|---|---|
| 64-88340 | 4/1989 | Japan | 250/339 |
| 8404665 | 12/1984 | PCT Int'l Appl. | 128/633 |
| WO90/09453 | 8/1990 | PCT Int'l Appl. | |
| 742776 | 6/1980 | U.S.S.R. | 250/339 |
| 2126717 | 3/1984 | United Kingdom | 128/633 |

OTHER PUBLICATIONS

Rigas et al., "Human Colon Adenocarcinoma Cell Lines Display Infrared Spectroscopic Features of Malignant Colon Tissues", Cancer Research, 52, Jan. 1992, pp. 84-88.

New Biotech, vol. 4, No. 6, pp. 5-7 (Jun. 1990), "Application for Pressurized FT-IR Spectroscopy".

Benedetti, E., et al., Leukemia Research, pp. 1001-1008, vol. 9, No. 8, 1985.

Andreolia, S. P., et al., The Journal of Pediatrics, Aug. 1986, pp. 292-297.

Jimbow, K., Cancer Research, vol. 44, pp. 1128-1134, (Mar. 1984).

Atanasov, A., Chemical Abstracts 75:31101m.

Kasama, K., The Journal of Biological Chemistry, vol. 264, No. 16, pp. 9453-9461 (Jun. 1989).

(List continued on next page.)

*Primary Examiner*—Carolyn E. Fields

[57] ABSTRACT

The presence of anomalies is detected in exfoliated cells (e.g. in a cervical smear) using infrared spectroscopy. A beam of infrared light is directed at specimens containing cells, which may be secretions, exudates, transudates, scrapings, brushings or otherwise obtained populations of exfoliated cells of various organs or tissues, and the anomaly is detected at at least one range of frequencies by determining whether changes in infrared absorption has occurred which is due to functional group vibration in, for example, phosphodiester groups of nucleic acids, COH groups of tissue proteins, carbohydrates, or due to special arrangements of lipid molecules or abnormal lipid structures, present in the specimen.

14 Claims, 6 Drawing Sheets

OTHER PUBLICATIONS

Lauer, J. L., et al., Proceedings of the 7th New Eng. Biorg. Conf., Troy, N.Y. (Mar. 1979), "Infrared Micro-Interferometer for Tissue Analysis", pp. 129–132.

Rougereau, A., et al., Internat. J. Vit. Nutr. Res. 57 (1987), pp. 19–23.

Wong, Patrick, T. T., et al., Biochemical and Biophysical Research Communications, 146, No. 1, pp. 232–238 (Jul. 1987).

Mushayakarara, E. C., et al., Biochemical and Biophysical Research Communications, vol. 134, No. 1, pp. 140–145 (Jan. 1986).

Mushayakarara, E. C., et al., Biochemia et Biophysica Acta, vol. 857, pp. 259–264 (1986).

Siminovitch, D. J., et al., Biochemia et Biophysica Acta, vol. 900, pp. 163–167 (1987), "High Pressure Infrared Spectroscopy of Lipid Bilayers: New Tests for Interdigitation".

Wong, Patrick T. T., et al., Applied Spectroscopy, vol. 44, No. 10, pp. 1715–1718 (1990).

Rigas, Basil, et al., Proc. Natl. Acad. Sci. USA, vol. 87, pp. 8140–8144, Oct. 1990.

METHOD OF DETECTING THE PRESENCE OF ANOMALIES IN EXFOLIATED CELLS USING INFRARED SPECTROSCOPY

BACKGROUND OF THE INVENTION

It is well known that examination for characteristic neoplastic cells in exfoliated tissue or cell specimens from, for example, the secretions, exudates, transudates, scrapings or brushings from various human organs or tissues may permit the diagnosis of malignancy. Exfoliative cytology has been found to be so valuable in the detection of early cancer of the uterus and uterine cervix that it is usually performed as a routine part of the annual examination for all adult women, see Pathologic Examination, Enfoliative Cytologic Study, Chapter 24, pages 362–365.

Exfoliated tissue or cell specimens may also be obtained from, for example, the trachea and bronchi, stomach, rectum and colon, urinary tract, serous sac fluids, cyst fluids, synovial fluids, glandular secretions and exudates. Methods for obtaining, collecting and, if necessary, preserving the specimens may vary according to the preference.

Each collected specimen is spread intact as an even layer over a clean microscope slide and submerged in, for example, an alcohol-ether fixative for about one hour. After being fixed, and without being allowed to dry, the layer is coated with glycerin and the whole sandwiched between two glass slides. The slides are then sent to a laboratory for staining and microscopic diagnosis by trained and experienced pathologists or cytologists.

While the microscopic diagnosis of exfoliated tissue or cell specimens is useful, the diagnostic interpretation:
i) has to be carried out by skilled personnel,
ii) is not completely reliable due, for example, to abundant mucous, trichomonas infection or atrophy, and
iii) cannot accurately detect, for example, malignancy in tissues or cells in the pre-malignant or early malignant stages.

There is a need for a method of detecting the presence of anomalies in exfoliated cells wherein:
i) a simple test on the specimen, and the interpretation thereof, can be carried out by personnel having no medical skills and after a relatively brief course of training,
ii) with proper care, interpretation of the test results is reliable, and
iii) malignancy in tissues or cells can be detected in the pre-malignant or early malignant stages.

It has already been proposed in the applicants' co-pending Canadian Patent Application No. 2,008,831-1, filed Jan. 29, 1990, "Method of Detecting the Presence of Anomalies in Biological Tissues and Cells in Natural or Cultured Form by Infrared Spectroscopy", P. T. T. Wong and B. Rigas, which corresponds to U.S. Pat. No. 5,038,039, to detect the presence of anomalies in biological tissues and cells in natural and cultured form (e.g. cancerous tissues or cells) by infrared spectroscopy. A beam of infrared light is directed at a sample of tissue or cells in natural or cultured form containing the cells to be tested, and the anomaly is detected at at least one range of frequencies by determining whether changes in infrared absorption have occurred due to the vibration of at least one functional group of molecules present in the sample which is characteristic of the anomaly.

The method taught by P. T. T. Wong and B. Rigas is applied in the examples to biopsed tissue or cultured cells. In particular, P. T. T. Wong and B. Rigas, page 7, line 20 to page 8, line 36, teach the detection of colorectal cancer from colonic mucosa immediately following bovel resection, i.e. colonic mucous membrane immediately following surgical removal of a section or segment of the bowel.

SUMMARY OF THE INVENTION

It has now been found, according to the present invention, that detection of the presence of anomalies in exfoliated cells by spectral analysis of the infrared absorption characteristics of the cells is possible. Mucin, water, inorganic salts, epithelial cells, red blood cells and leukocytes of the fluid do not give rise to any spurious interpretation of the infrared spectral absorption characteristics of the cells.

According to the present invention there is provided a method of detecting the presence of anomalies in exfoliated cells using infrared spectroscopy, comprising:
a) directing a beam of infrared light at a specimen of exfoliated cells, and
b) determining if an anomaly is present in the specimen by spectral analysis of the infrared absorption of the specimen, at at least one range of frequencies, to ascertain whether at least one change in the infrared absorption characteristics has occurred, due to vibration of at least one functional group of molecules, in the specimen, which is characteristic of that anomaly.

The said at least one change in the infrared absorption characteristics may be a change in absorption intensity at a particular frequency, a change of frequency at which a particular absorption occurs, or a different pressure applied to the functional group causing a change of frequency at which a particular absorption occurs.

The functional group of molecules may be in at least one of the following molecules, carbohydrates, nucleic acids, tissue proteins or membrane lipids.

The functional group may be a phosphodiester group in nucleic acids, a C—OH group in tissue protein and carbohydrates, or a $CH_2$ group in lipids.

The functional group may be at least one functional group selected from the groups consisting of carbohydrates, phosphodiester groups in nucleic acids, COH groups of tissue proteins or carbohydrates and $CH_2$ group of lipids.

The specimen may be a Papanicolau smear.
The specimen may be a cervical specimen.
The specimen may be an endocervical specimen.
The specimen may be an ectocervical specimen.
The specimen may be a vaginal specimen.
The specimen may be a uterus specimen.

BRIEF DESCRIPTION OF THE DRAWING

In the accompanying drawings which illustrate, by way of example, embodiments of the present invention.

DESCRIPTION OF THE PREFERRED EMBODIMENTS

Figure 1:
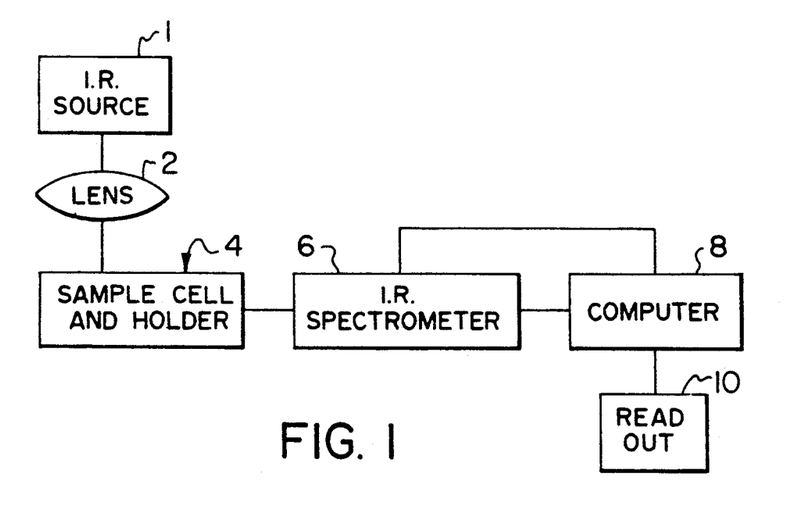
FIG. 1 is a block diagram of an apparatus for detecting the presence of anomalies in exfoliated cells using infrared spectroscopy.

Referring now to FIG. 1, there is shown an infrared source 1, a lens 2, a sample cell and holder 4, an infrared spectrometer 6, a computer 8 and a readout 10.

In operation, an exfoliated tissue or cell specimen is placed in the sample cell and holder 4 and a beam of infrared light from the source 1 which has been condensed by the lens 2, is passed through the sample in the sample cell and holder 4. Any infrared absorption by the specimen is detected by the infrared spectrometer 6, which in turn is computed by the computer to give a readout at the readout 10. The computer readout may be arranged to directly indicate whether the specimen is a normal, healthy one or one which contains an anomaly (i.e. benign, dysplasia or malignant).

In tests to verify the present invention, infrared (IR) spectra were obtained as described with reference to FIG. 1 from exfoliated cervical cell specimens, that were collected from 25 females undergoing a surveillance Papanicolaou test (cervical cytology) following a standard "scraping" or "brushing" procedure. These specimens consisted of epithelial cells, inflammatory cells, red blood cells and bacteria that are part of the normal flora. The tests indicated that non-epithelial cells, present in varying numbers in all specimens and semiquantitated by two independent observers, did not influence the infrared spectra to any significant extent in the spectral regions under study; hemolysis of the red cells studied in control specimens did not significantly alter the infrared spectra either in the spectral region under study.

In further tests, cells from exfoliated scrapings obtained with a brush, were harvested by gently shaking the brush in a normal saline solution. Two halves of this cell suspension were separately pelleted by centrifugation. Following removal of the supernatant, one pellet was frozen in liquid nitrogen, to be studied later spectroscopically for IR absorption, according to the present invention, while aliquots of the other pellet were spread on microscope slides, fixed and stained with Papanicolaou stain and diagnosed in the conventional manner. Each sample was rated independently by two experienced physicians, and there was complete agreement between these ratings. Infrared absorption spectra were obtained as previously described with reference to FIG. 1. Cells were smeared on the sample holder; the spectroscopic patterns were stable for many hours following sample application. An auto scale plotting configuration device was set to automatically normalize peak intensities.

The tests made fell into two groups, which were i) atmospheric pressure tests, where the sample holder described and claimed in U.S. Pat. No. 4,980,551, dated Dec. 25, 1990, was found to be useful, and ii) high pressure tests, where the sample holder described and claimed in U.S. Pat. No. 4,970,396, dated Nov. 13, 1990, was found to be useful.

Figure 2:
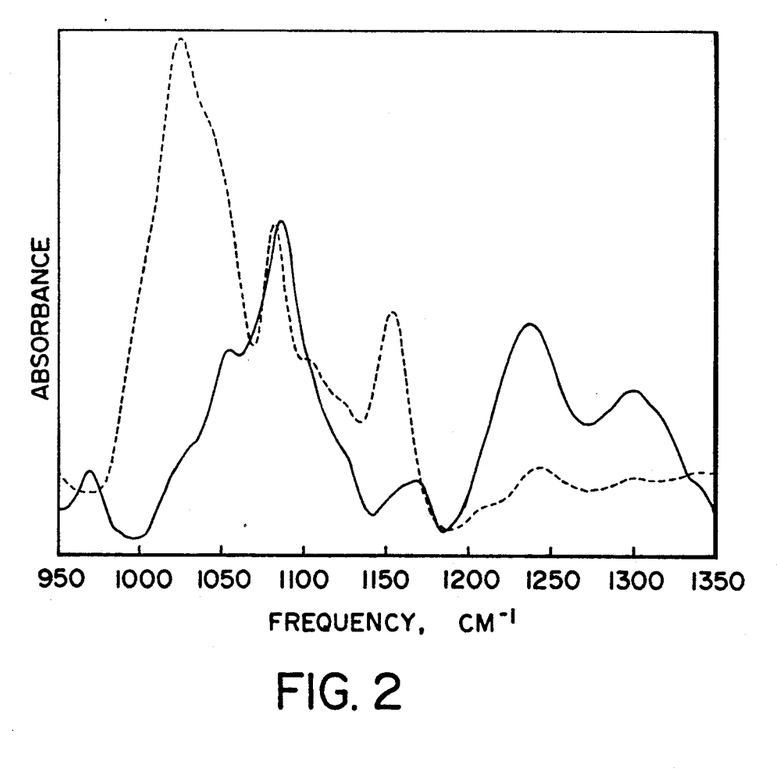
FIG. 2 shows infrared spectra in the frequency range 950 to 1,350 $cm^{-1}$, obtained from normal healthy, exfoliated cervical cell specimens designated - - - and from exfoliated cervical cell specimens designated — and diagnosed in a conventional, cytological manner as malignant.

Cervical specimens rated as normal healthy specimens on the basis of conventional, cytological evaluation displayed essentially identical IR spectra. The spectra of specimens diagnosed cytologically as malignant were markedly different from those of normal specimens. In FIG. 2 the results for normal healthy cervical tissue are shown - - - , and the results for malignant cervical tissue are shown ——, these are typical spectra from normal healthy and malignant cervical specimens. The most prominent differences include the following findings in malignant specimens:

a) severe change in the intensity of the bands at $\sim 1025$ cm$^{-1}$, $\sim 1047$ cm$^{-1}$ (it appears as a shoulder on $\sim 1025$ cm$^{-1}$ band), $\sim 1082$ cm$^{-1}$, $\sim 1155$ cm$^{-1}$, $\sim 1244$ cm$^{-1}$ and $\sim 1303$ cm$^{-1}$, b) significant shift of $\sim 1082$ cm$^{-1}$, $\sim 1155$ cm$^{-1}$ and $\sim 1244$ cm$^{-1}$ peaks, and c) a new band peaking at $\sim 970$ cm$^{-1}$.

Figure 3:
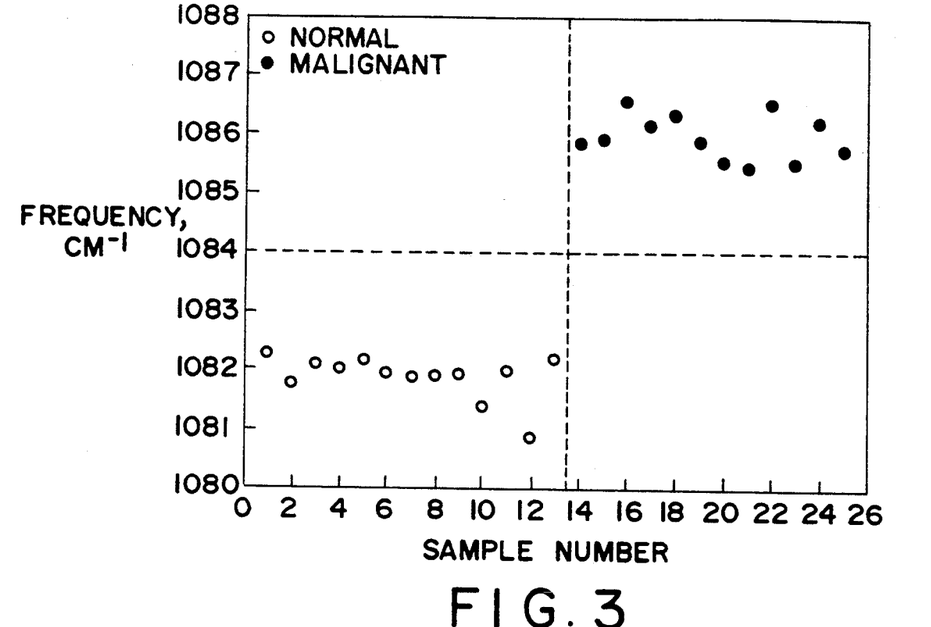
FIGS. 3 to 5 show the frequency shifts of the infrared bands at $\sim 1082$ cm$^{-1}$, and $\sim 1155$ cm$^{-1}$, and the changes in the intensity ratios between the infrared band at $\sim 1025$ cm$^{-1}$ and $\sim 1082$ cm$^{-1}$, respectively, between healthy, exfoliated cervical cell specimens and those diagnosed in a conventional, cytological manner as malignant.
Figure 4:
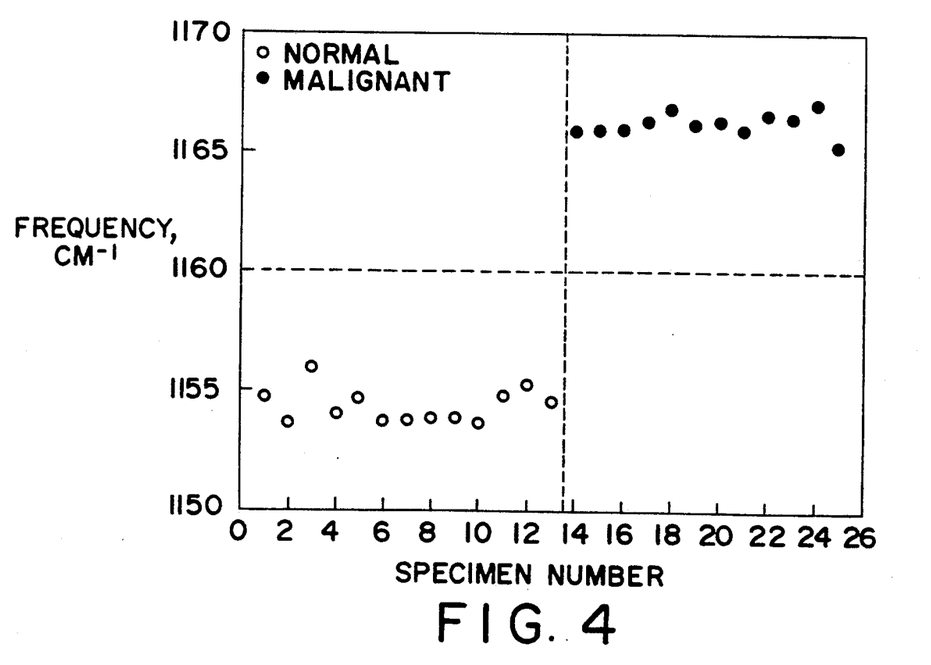
Figure 5:
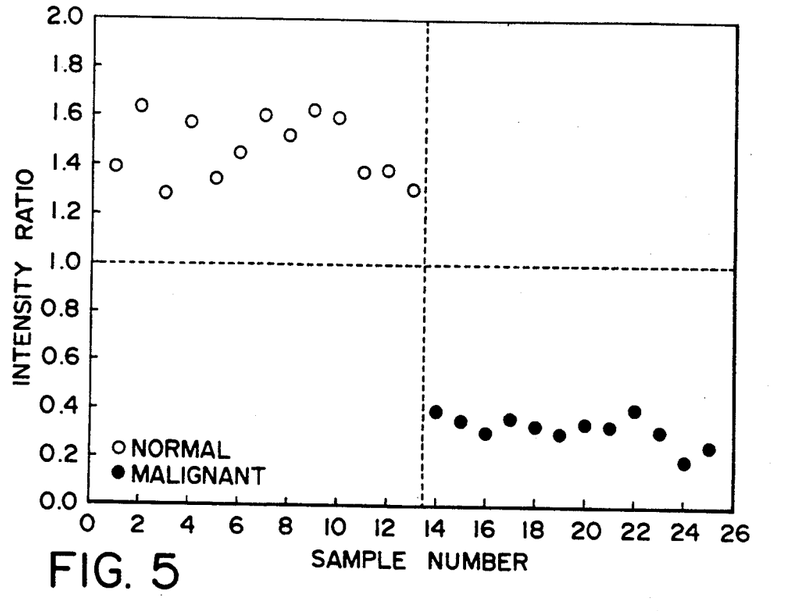

In FIGS. 3 to 5, O are the results for normal healthy exfoliated cervical tissue and ● are the results for malignant, exfoliated cells of cervical tissue. The shifts in the two peaks at $\sim 1082$ cm$^{-1}$ and $\sim 1155$ cm$^{-1}$ averaging about 4 and 12 wave numbers, respectively, for all the specimens studied are shown in FIGS. 3 and 4. FIG. 5 shows that the ratio of the peak intensity between the $\sim 1025$ cm$^{-1}$ and $\sim 1082$ cm$^{-1}$ bands differs greatly between normal and cancer tissue specimens.

The bands at $\sim 1025$ cm$^{-1}$ and $\sim 1047$ cm$^{-1}$ were found to be due to carbohydrates, and glycogen was found to make an overwhelming contribution to the intensity of these bands. The bands at ~1082 cm$^{-1}$ and ~1244 cm$^{-1}$ were found to be due to the symmetric and asymmetric phosphate (PO$^-_2$) stretching modes, respectively. They were found to originate mainly in the vibrations of the phosphodiester groups of cellular nucleic acids. The band at ~1155 cm$^{-1}$ was found to be due to the C-O stretching mode of the C—OH groups of, among others, the residues of the amino acids serine, threonine and tyrosine in cell proteins as well as the C—OH groups of carbohydrates. The band at ~1303 cm$^{-1}$ consists of many overlapping bands and its assignment has yet to be confirmed. Finally, the band at ~970 cm$^{-1}$ was found to be due partly to the vibrational mode of dianionic phosphate groups, as had been previously observed in the infrared spectra of model phosphorylated proteins, and partly due to DNA and/or RNA molecules.

Figure 6:
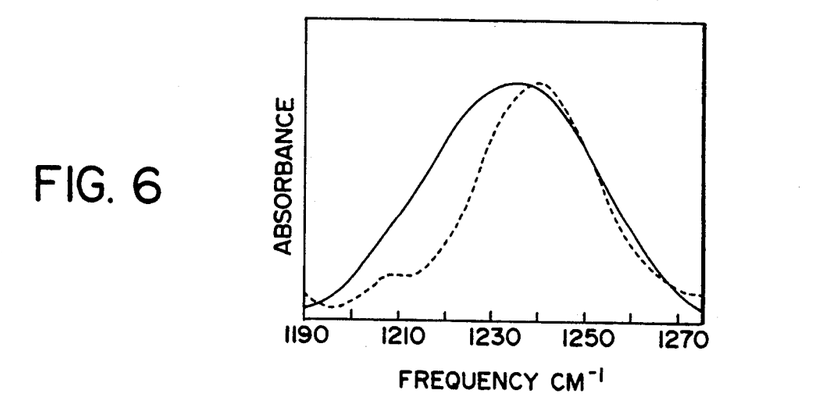
FIG. 6 shows the infrared spectra depicted in FIG. 2, for the bands at $\sim 1240$ cm$^{-1}$, enlarged and superimposed.
Figure 7:
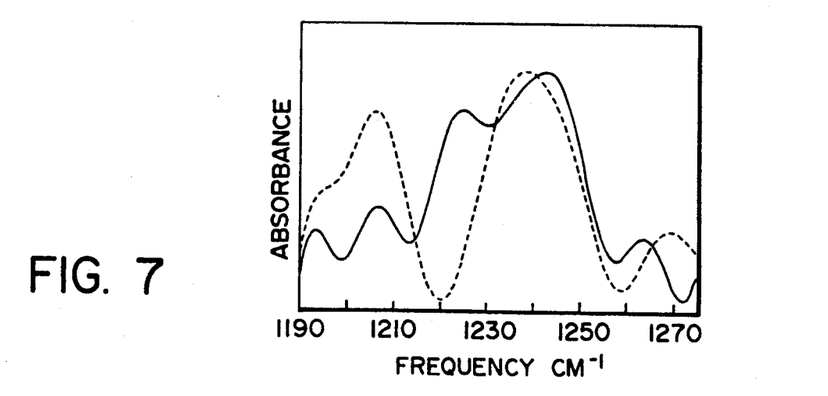
FIG. 7 shows the corresponding third power derivative spectra of the infrared spectra depicted in FIG. 2 for the bands in the frequency region 1190 to 1275 cm$^{-1}$.
Figure 8:
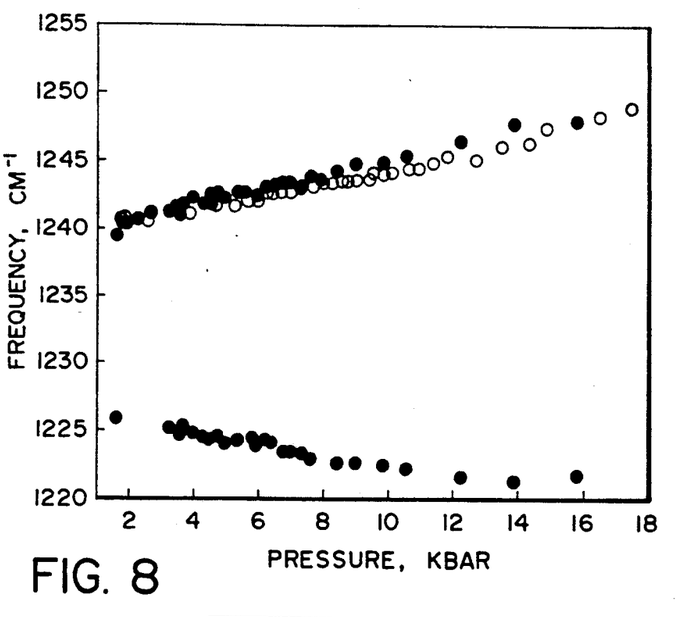
FIG. 8 shows a comparison of the pressure dependencies of the vibrational frequencies of $PO_2$ groups of nucleic acids in exfoliated cells of cervical tissues.

Referring now to FIG. 6, which is an enlargement of a portion of FIG. 2, and the corresponding third power derivative spectra shown in FIG. 7, a more detailed study of the asymmetric phosphate stretching band revealed that in malignant, exfoliated cervical tissues, shown ——, it consisted of two overlapping bands, one of which, the lower frequency band, was markedly increased when compared to normal healthy, exfoliated cells. The frequency of the asymmetric PO$^-_2$ stretching band was known at the time that the tests were made to be ~1220 cm$^{-1}$, when the PO$^-_2$ group was fully hydrogen-bonded, and greater than ~1240 cm$^{-1}$ when it is not hydrogen-bonded. This finding indicated that in cervical cancer many PO$^-_2$ groups of nucleic acids are hydrogen-bonded, in contrast to those of the normal, exfoliated cervical tissue. This conclusion is supported further by the pressure dependence of the frequencies of these bands, as shown in FIG. 8, where O shows the results for normal healthy, exfoliated cervical tissue and ● the results for cancerous, exfoliated cervical tissue. The frequency of the low-frequency band was found to decrease with increasing pressure, whereas that of the high-frequency band of cancer and the single PO$^-_2$ band of normal healthy tissue were found to increase with increasing pressure. This response of the low-frequency band to pressure is known to be typical of a hydrogen-bonded group because pressure enhances the strength of hydrogen bonds and thereby decreases the frequency of the PO$^-_2$ stretching. On the other hand, the effect of pressure on the high-frequency PO$^-_2$ band, common to malignant and normal tissue, is known to be characteristic of non-hydrogen bonded functional groups and results from pressure enhancement of intermolecular interactions.

Figure 9:
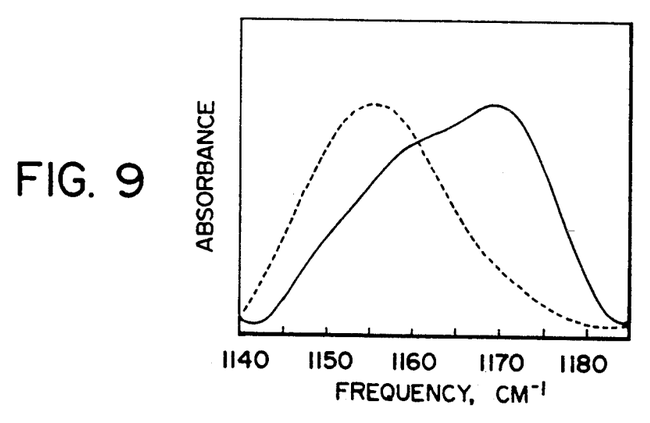
FIG. 9 is an enlargement of the infrared bands in the frequency region 1140 cm$^{-1}$ to 1185 cm$^{-1}$ between normal, healthy exfoliated cervical cell specimens and those diagnosed in a conventional, cytological manner as malignant.
Figure 10:
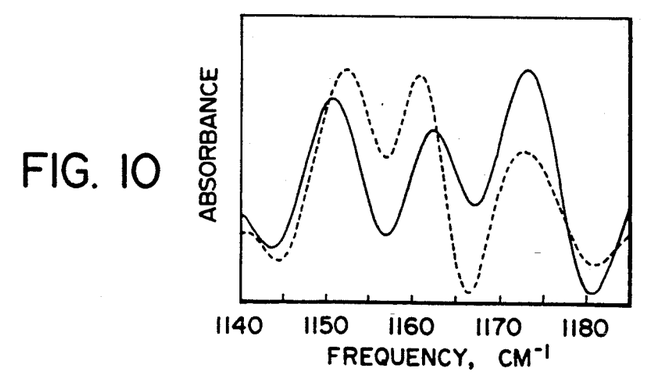
FIG. 10 shows the corresponding third power derivative spectra of the infrared spectra shown in FIG. 9.
Figure 11:
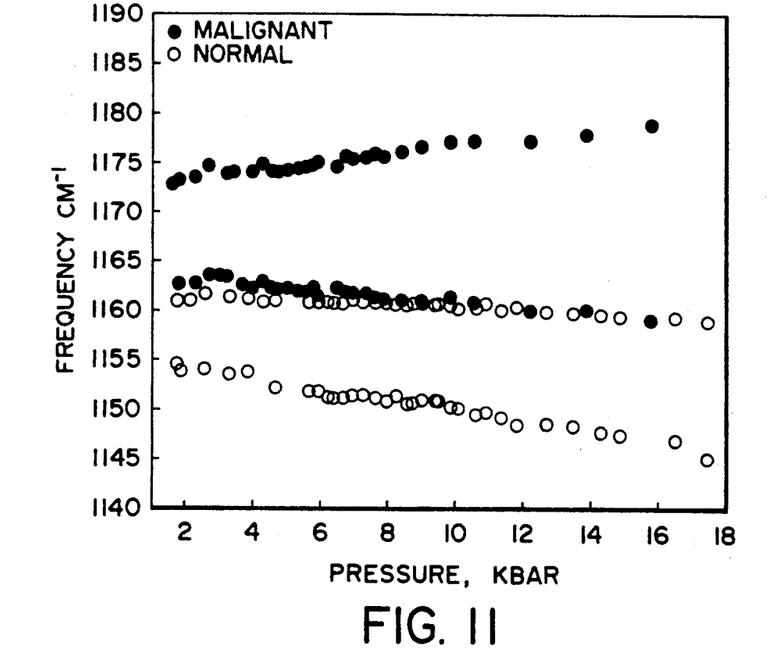
FIG. 11 shows a comparison of the pressure dependancies of the frequencies of the component bands of the C-O stretching modes in the frequency range 1140 cm$^{-1}$ to 1190 cm$^{-1}$ between normal, healthy, exfoliated cervical tissue specimens and those diagnosed in a conventional, cytological manner as malignant.

A similar analysis of the C-O stretching band at 1155 cm$^{-1}$, shown in FIGS. 9 and 10 where the results for normal, healthy, exfoliated cells of cervical tissue are shown - - - and the results for cancerous, exfoliated cells of cervical tissue are shown —, revealed that it consists of three overlapping bands, ~1153 cm$^{-1}$, ~1161 cm$^{-1}$ and ~1172 cm$^{-1}$ of which the first two display decreased intensity and the third increased intensity when compared to the corresponding bands of normal cervical tissue. The frequencies of the first two decrease with increasing pressure, whereas that of the latter was found to increase as shown in FIG. 11. These findings, therefore, indicate that the component bands at ~1153 cm$^{-1}$ and ~1161 cm$^{-1}$ arise from the stretching vibrations of hydrogen-bonded C—OH groups, whereas the band at ~1172 cm$^{-1}$ is due to the stretching vibrations of non hydrogen-bonded C—OH groups.

Figure 12:
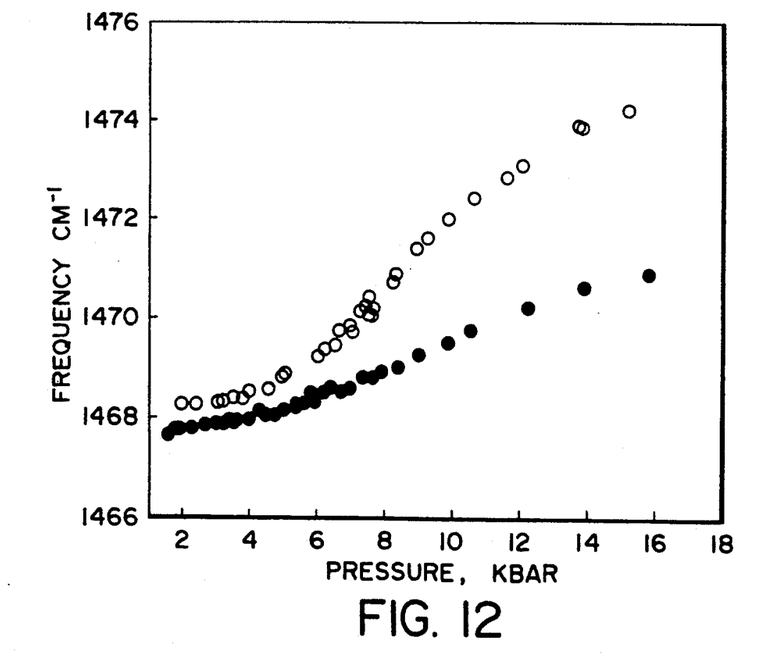
FIG. 12 shows a comparison of the pressure dependancies of the $CH_2$ bending modes of the methylene chains in membrane lipids between normal exfoliated cervical tissue specimens and those diagnosed in a conventional, cytological manner as malignant.

In FIG. 12, where O shows the results for normal, healthy, exfoliated cells of cervical tissue and ● shows the results for cancerous, exfoliated cells of cervical tissue, the pressure dependence of the frequency of the CH$_2$ bending mode of the methylene chains of lipids is shown in the frequency range 1466 cm$^{-1}$ to 1476 cm$^{-1}$. The pressure dependence in the frequency of this band has previously been widely used to study interchain packing and order/disorder properties of lipid bilayers. In lipid bilayers pressure was found to produce an increase in the frequency of this band because induced conformational and orientational ordering of the methylene chains occurred, which thereby increase interchain interactions. In malignant cervical tissue, pressure was found to induce a smaller shift in this frequency range as compared to normal healthy tissue. This indicates that in exfoliated cells of cervical cancer tissue the methylene chains of lipids are more disordered than in normal, healthy, exfoliated cells of cervical tissue.

Figure 13:
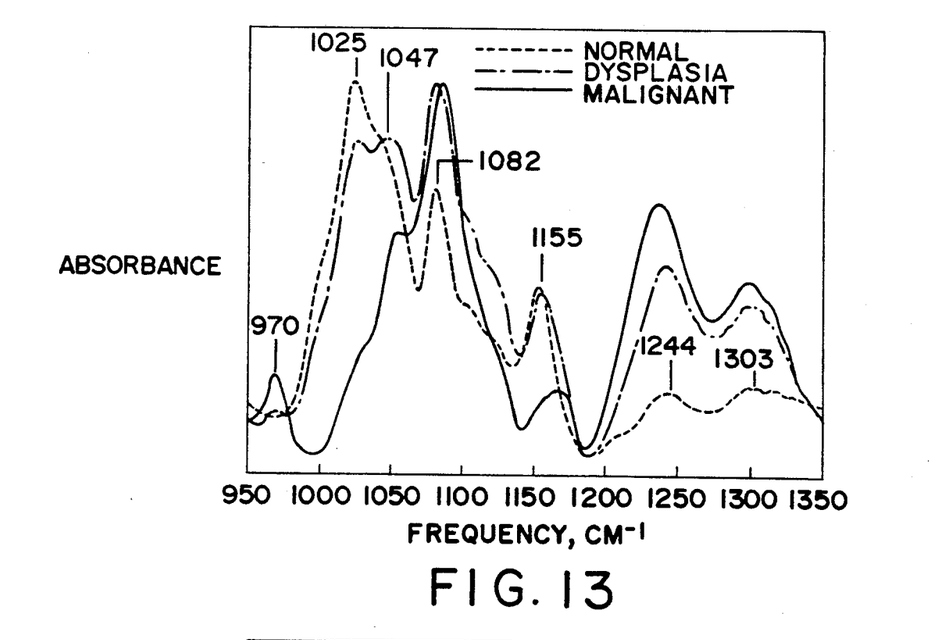
FIG. 13 shows a comparison of the infrared spectra in the frequency range 950 cm$^{-1}$ to 1350 cm$^{-1}$ for exfoliated cervical specimens diagnosed in a conventional, cytological manner as normal, malignant and dysplasia.

In FIG. 13, the results for normal, healthy, exfoliated cervical specimens are shown - - -, for dysplasia are shown -.-., and for malignant specimens are shown —.

In FIG. 13, the prominent differences for dysplasia specimens as compared to normal specimens, include:
a) severe change in the intensity of the bands at ~1025 cm$^{-1}$, ~1082 cm$^{-1}$, ~1244 cm$^{-1}$ and ~1303 cm$^{-1}$, and
b) a significant shift in the frequency of the bands at ~1047 cm$^{-1}$ and ~1082 cm$^{-1}$.

Also in FIG. 13, the prominent differences for malignant specimens as compared to normal and dysplasia specimens include:
a) severe change in the intensity of the bands at ~970 cm$^{-1}$, ~1025 cm$^{-1}$, ~1047 cm$^{-1}$, ~1082 cm$^{-1}$, [1155 cm$^{-1}$, ~1244 cm$^{-1}$ and ~1303 cm$^{-1}$, and
b) a significant shift in the frequency of the bands at ~1025 cm$^{-1}$, ~1047 cm$^{-1}$, ~1082 cm$^{-1}$ and ~1155 cm$^{-1}$.

These tests indicated that several important changes are associated with cervical, exfoliated cancer tissue. The amount of glycogen was found dramatically decreased in exfoliated, cervical cells of cancer tissue as compared to normal, healthy, exfoliated cells of cervical tissue. This is further confirmed by the fact that cancer of the liver, an organ extremely rich in glycogen, displays a similar spectroscopic pattern which is not observed in cancer of the colon, an intestinal portion poor in glycogen.

Figure 14:
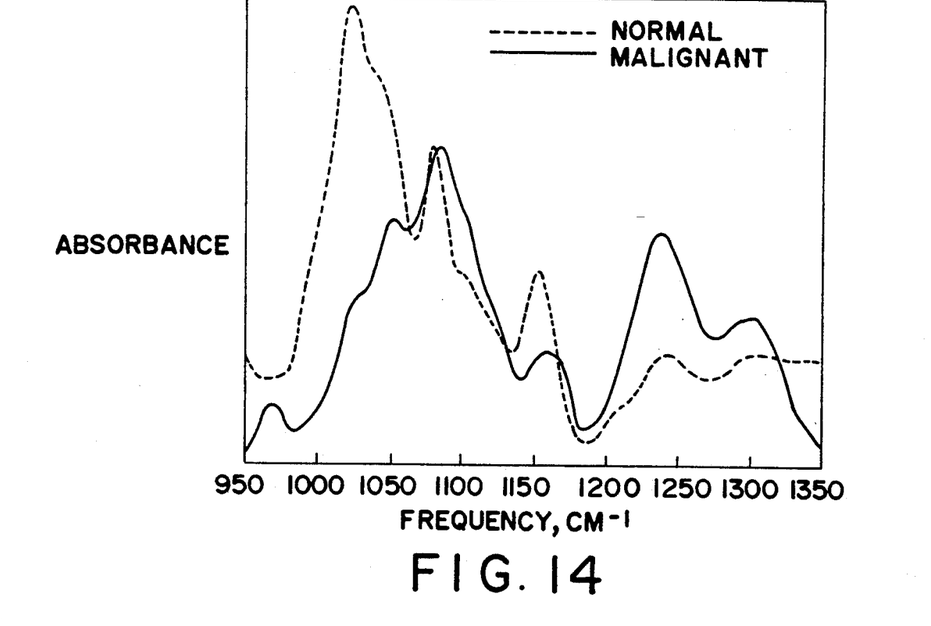
FIG. 14 shows infrared spectra in the frequency range 950 to 1,350 cm$^{-1}$, obtained from healthy, exfoliated vaginal cell specimens and those diagnosed in a conventional, cytological manner as malignant.

The known spectrum of glycogen (D-glycogen from mammalian liver) is comparable with that obtained by the applicants in the frequence region ~975-1100 cm$^{-1}$ (FIGS. 13 and 14).

Furthermore, the hydrogen-bonding of the phosphodiester groups of nucleic acids was found to increase in exfoliated cells of cervical cancer tissue. This spectroscopic finding was common to those found in other tests with cancerous tissue biopsied specimens that the applicants had examined such as colon, liver, skin, vagina and breast.

In FIG. 14, the results for healthy vaginal specimens are shown - - -, while those for malignant specimens are shown —.

In FIG. 14, the prominent differences for the malignant specimens as compared to normal specimens include:

a) a severe change in the intensity of the bands at ~1025 cm$^{-1}$, ~1154 cm$^{-1}$, ~1240 cm$^{-1}$ and ~1300 cm$^{-1}$, and b) a significant shift in the frequency of the bands at ~1025 cm$^{-1}$, ~1155 cm$^{-1}$ and ~1081 cm$^{-1}$.

These and other tests have indicated that the present invention is useful for, for example, detecting anomalies in exfoliated tissue or cell specimens from secretions, exudates, transudates of various human or other mammalian organs or tissues, and is particularly useful for detecting exfoliated cancerous tissues or cells from Papanicolaou cervical smears, i.e., endocervical smears, ectocervical smears, vaginal smears and uterus smears.

Exfoliated cell anomalies which may be detected according to the present invention include, for example, viruses, bacteria, fungi and other infections and non-infectious diseases.

The cell anomalies may be detected in exfoliated cells or in cells in exfoliated tissue.

We claim:

1. A method of detecting the presence of anomalies in exfoliated cells using infrared spectroscopy, comprising:
    a) directing a beam of infrared light at a specimen of exfoliated cells, and
    b) determining if an anomaly is present in the specimen by spectral analysis of the infrared absorption by the specimen, at at least one range of frequencies, to ascertain whether at least one change in the infrared absorption characteristics has occurred, due to vibration of at least one functional group of molecules, present in the specimen, which is characteristic of that anomaly.

2. A method according to claim 1, wherein the said at least one change in the infrared absorption characteristics is a change in absorption intensity at a particular frequency, a change of frequency at which a particular absorption occurs, or a different pressure applied to the functional group causing a change of frequency at which a particular absorption occurs.

3. A method according to claim 1, wherein the at least one functional group of molecules is in at least one of molecules selected from the group consisting of carbohydrates, nucleic acids, tissue proteins and membrane lipids.

4. A method according to claim 1, wherein the at least one functional group of molecules is selected from the group consisting of a phosphodiester group in nucleic acids, a C-OH group is tissue protein and carbohydrates, and a CH$_2$ group in lipids.

5. A method according to claim 1, wherein the at least one functional group of molecules is in at least one member selected from the group consisting of carbohydrates, phosphodiester group in nucleic acids, C-OH groups of tissue proteins and carbohydrates, and CH$_2$ group of lipids.

6. A method according to claim 1, wherein the specimen is a Papanicolau smear.

7. A method according to claim 1, wherein the specimen is a cervical specimen.

8. A method according to claim 1, wherein the specimen is an endocervical specimen.

9. A method according to claim 1, wherein the specimen is an ectocervical specimen.

10. A method according to claim 1, wherein the specimen is a vaginal specimen.

11. A method according to claim 1, wherein the specimen is a uterus specimen.

12. A method according to claim 1, wherein said at least one range of frequencies is in the range of from 950 cm$^{-1}$ to 1476 cm$^{-1}$.

13. A method according to claim 1, wherein said at least one range of frequencies is in the range of from 950 cm$^{-1}$ to 1350 cm$^{-1}$.

14. A method according to claim 1, wherein said at least one change in the infrared absorption characteristics is a change of frequency at which a particular absorption occurs, or a different pressure applied to the functional group causing a change of frequency at which a particular absorption occurs.

* * * * *

UNITED STATES PATENT AND TRADEMARK OFFICE
CERTIFICATE OF CORRECTION

PATENT NO. : 5,168,162

DATED : December 1, 1992

INVENTOR(S) : PATRICK T.T. WONG ET AL

It is certified that error appears in the above-identified patent and that said Letters Patent is hereby corrected as shown below:

item [75]
    On the Title page, change the first listed inventor from "Patrick T.T. Oong" to -- Patrick T.T. Wong --.

On the Title page, add item   [30] Foreign Application Priority Data

Feb. 04, 1991 [CA] Canada . . . . . . . . . . . 2,035,603 --.

Signed and Sealed this

Nineteenth Day of October, 1993

Attest:

BRUCE LEHMAN

*Attesting Officer*      *Commissioner of Patents and Trademarks*